(12) United States Patent
Luo et al.

(10) Patent No.: US 9,133,513 B2
(45) Date of Patent: Sep. 15, 2015

(54) HIGH THROUGHPUT METHYLATION DETECTION METHOD

(75) Inventors: Huijuan Luo, Guangdong (CN); Guanyu Ji, Guangdong (CN); Hui Jiang, Guangdong (CN); Mingzhi Wu, Guangdong (CN); Jihua Sun, Guangdong (CN); Renhua Wu, Guangdong (CN); Junwen Wang, Guangdong (CN); Fei Gao, Guangdong (CN)

(73) Assignee: BGI TECH SOLUTIONS CO., LTD., Shenzhen (CN)

( * ) Notice: Subject to any disclaimer, the term of this patent is extended or adjusted under 35 U.S.C. 154(b) by 0 days.

(21) Appl. No.: 14/119,266

(22) PCT Filed: May 22, 2012

(86) PCT No.: PCT/CN2012/075919
§ 371 (c)(1),
(2), (4) Date: Jan. 3, 2014

(87) PCT Pub. No.: WO2012/159564
PCT Pub. Date: Nov. 29, 2012

(65) Prior Publication Data
US 2014/0256563 A1    Sep. 11, 2014

(30) Foreign Application Priority Data
May 23, 2011   (CN) .......................... 2011 1 0133858

(51) Int. Cl.
*C12N 15/10*   (2006.01)
*C12Q 1/68*    (2006.01)
*C40B 50/06*   (2006.01)

(52) U.S. Cl.
CPC .......... *C12Q 1/6874* (2013.01); *C12N 15/1065* (2013.01); *C12Q 1/6806* (2013.01); *C12Q 1/6869* (2013.01); *C40B 50/06* (2013.01)

(58) Field of Classification Search
None
See application file for complete search history.

(56) References Cited

U.S. PATENT DOCUMENTS

| 2009/0148842 A1* | 6/2009 | Gormley et al. .................. 435/6 |
| 2013/0295569 A1* | 11/2013 | Evans et al. .................. 435/6.11 |

FOREIGN PATENT DOCUMENTS

| CN | 102409408 | 4/2012 |
| WO | 03/035860 | 5/2003 |
| WO | 03/087774 | 10/2003 |
| WO | 2005/090607 | 9/2005 |

OTHER PUBLICATIONS

Tewhey et al (2009) "Enrichment of sequencing targets from the human genome by solution hybridization" Genome Biology 10:R116.*
Albert et al., Direct selection of human genomic loci by microarray hybridization, Nature Publishing Group, 2007.

* cited by examiner

*Primary Examiner* — Tracy Vivlemore
*Assistant Examiner* — Karen S Weiler
(74) *Attorney, Agent, or Firm* — Hodgson Russ LLP

(57) ABSTRACT

Provided is a high throughput methylation detection method, particularly a combined sequence capture and bisulfite sequencing method. The method accurately and effectively analyzes the methylation status of the target area in several samples simultaneously, lowers the difficulty of probe design, enhances operation and application feasibility, and enables high throughput methylation detection of high accuracy on interested target sequences and areas in a complete genome. The method is targeted and conserves energy and time.

22 Claims, 4 Drawing Sheets

HIGH THROUGHPUT METHYLATION DETECTION METHOD

CROSS-REFERENCE TO RELATED APPLICATION

This application claims priority to and benefits of Chinese Patent Application Serial No.201110133858.1, filed with the State Intellectual Property Office of P. R. China on May 23, 2011, the entire content of which is incorporated herein by reference.

FIELD

The present disclosure relates to a field of high-throughput genomic methylated DNA detection, and more particularly to a method combining sequence capturing with bisulfite sequencing. In addition, the present disclosure also relates to a field of exome sequencing and a methylation sequencing technology based on bisulfite conversion. The present disclosure still relates to a methylated index adaptor technology, which may perform sequence capturing of several samples simultaneously on one chip. The method of present disclosure is particularly suitable for Next-Generation sequencing technology, especially Solexa sequencing technology.

BACKGROUND

DNA methylation is one of the most research focuses in epigenetics field, and also gradually becomes epigenetic marker of several diseases, such as mammalian development and cancer. DNA methylation not only plays important roles in structural modification of chromosome and genome stability, but also involves in several biological process in eukaryote, for example developments of several diseases such as embryonic development, genomic imprinting, X chromosome inactivation, regulation and silence of gene expression, silence of retrotransposon and mammalian tumor (Brena R M et al. 2006; Egger G et al. 2004; Gu H et al. 2010, which are all incorporated herein by reference). Methylated DNA biomarker provides a large number of reference information for early evaluation of several diseases comprising detection evaluation of individual with high risk.

SUMMARY

Embodiments of the present disclosure seek to solve at least one of the problems existing in the prior art to at least some extent.

Thus, the present disclosure provides means which may determine a methylation information in a nucleic acid sample.

In one aspect of the present disclosure, there is provided a method of constructing a sequencing-library. According to embodiments of the present disclosure, the method may comprise: fragmenting a nucleic acid sample, to obtain a nucleic acid fragment; ligating the nucleic acid fragment to an adaptor, to obtain a nucleic acid fragment ligated to the adaptor; subjecting the nucleic acid fragment ligated to the adaptor to sequence capturing using a probe, to obtain a nucleic acid fragment from a predetermined region; subjecting the nucleic acid fragment from the predetermined region to a bisulfite treatment, to convert an unmethylated cytosine in the nucleic acid fragment from the predetermined region to a uracil, to obtain a converted nucleic acid fragment; and amplifying the converted nucleic acid fragment, to obtain an amplified product, wherein the amplified product constitutes the sequencing-library. The sequencing-library constructed by the method of constructing the sequencing-library according to embodiments of the present disclosure, may be effectively used to determine the methylation information of the nucleic acid sample.

In another aspect of the present disclosure, there is provided a sequencing-library. The sequencing-library is constructed by the method of constructing the sequencing-library above-mentioned. The sequencing-library according to embodiments of the present disclosure may be effectively used to determine the methylation information of the sequencing-library.

In an additional aspect of the present disclosure, there is provided a method of determining a methylation information of a nucleic acid sample. According to embodiments of the present disclosure, the method may comprise: constructing a sequencing-library for the nucleic acid sample according to the method of the above-mentioned method; sequecing the sequencing-library, to obtain a sequencing result; and determining the methylation information of the nucleic acid sample based on the sequencing result. Thus, the method of the present disclosure may effectively determine the methylation information of the nucleic acid sample. According to embodiments of the present disclosure, the sequencing is performed by using a Next-Generation sequencing platform, and preferably the sequencing is performed by using a Solexa sequencing platform.

In a further aspect of the present disclosure, there is provided use of the sequencing-library according to embodiments of the present disclosure in determining a methylation information of a nucleic acid sample.

In a still another aspect of the present disclosure, there is provided a method of determining a methylation distribution information of an exome in a human whole genome. According to embodiments of the present disclosure, the method may comprise: constructing a sequencing-library of the exome for the human whole genome DNA according to the method above-mentioned; sequencing the sequencing-library, to obtain a sequencing result; and determining the methylation distribution information of the exome in the human whole genome based on the sequencing result. The method according to embodiments of the present disclosure may effectively determine the methylation distribution information of the exome in the human whole genome.

Thus, according to embodiments of the present disclosure, aiming at the problems existing in the prior art of methylation research method based on bisulfite, a method is provided that combines sequence capturing and bisulfite sequencing, and this method may be used to capture target regions from a plurality of samples in one sequence capturing experiment, which may effectively and accurately analyze methylation information of the target region, decrease difficulties of designing probe, and increase the feasibility of operation and application, and then enables high-throughput and high-accuracy detection of methylation of target sequence and region of interest in the whole genome. Moreover, the method also has a characteristic of high specificity with low cost and high efficiency.

The target region referred herein is exon region. A technique combining exome capturing with bisulfite sequencing, which may be used to detect a methylation distribution information of an exome in a human whole genome, has broad application value in studying the role of exon in regulating gene expression.

According to embodiments of the present disclosure, the technique may comprise: randomly breaking genomic DNA; ligating a specific adaptor; sequence capturing using a liquid-phase hybridization platform; adding exogenous DNA to the captured DNA; subjecting the captured DNA to the bisulfite treatment; subjecting the treated DNA to PCR amplification; assaying the effect of the bisulfite treatment by TA cloning; subjecting a library to quantitative assay; high-throughput sequencing using a Next-Generation sequencing platform; and determining a highly-accurate methylation information within a specific region. According to embodiments of the present disclosure, the technical solution may be comprised of: selection of probe for sequence capturing, library construction, sequence capturing, bisulfite treatment, sequencing on computer and data analysis.

Probe Selection for Sequence Capturing

In the present technical solution, designing probe is simple, which may be based on a liquid-phase or solid-phase hybridization chip. The probe may have a length of 60 mer to 120 mer. For example, a probe (SureSelect Human All Exon 38M kit (Agilent)) is selected, which covers whole exon region and a part of miRNA region in human, and is complementary to one of double strands in the target region in the genome, and has an average length of 120 mer.

Library Construction

Step 1. fragmentation of genomic DNA sample and exogenous genomic DNA

The initial target research material and the DNA material as the exogenous genome may be a genomic DNA from any species (for example, human genomic DNA, plant genomic DNA or insect genomic DNA). The genomic DNA is fragmented to obtain a nucleic acid fragment having a length of 200 bp to 300 bp using a physical or chemical method, such as an ultrasound fragmentation method. The exogenous genomic DNA preferably is a genomic DNA without modification of methylation, which plays role in effectively being co-treated with the sample during the bisulfite treatment, protecting a trace of DNA fragment, and maximize the reduction of trace DNA damage by the bisulfite treatment.

5 μg of intact genomic DNA without any contaminations such as protein and RNA, and λDNA as the exogenous genome are subjected to fragmenting, to obtain a nucleic acid fragment having a length of 200 bp to 300 bp using the ultrasound fragmentation method.

Step 2. end-repairing of nucleic acid fragment

After recycled and purified, the nucleic acid fragment is end-repaired using T4 DNA polymerase, Klenow fragment and T4 polynucleotide kinase, to obtain an end-repaired nucleic acid fragment. Then, a base A is added to the end-repaired nucleic acid fragment at 3'-end using Klenow fragment (3'-5' exo-) polymerase and dATP.

Step 3. ligation of PEI (Paired-end Index) methylated adaptor, also known as double-end index methylated adaptor The nucleic acid fragment having the base A at 3'-end is ligated to an adaptor specially designed and modified with methylation (at C site) using T4 DNA Ligase, to obtain the nucleic acid fragment ligated to the above adaptor. Then, the nucleic acid fragment ligated to the above adaptor is purified and recycled. For example, DNA is recycled from a purifying reaction system using MiniElute PCR Purification Kit (Qiagen). Then, DNA is subjected to quantification using methods such as Qubit (Invitrogen).

Sequence Capturing

500~1000 ng of the nucleic acid fragment ligated to the adaptor is subjected to sequence capturing on a liquid-phase or solid-phase hybridization platform, such as Agilent liquid-phase hybridization platform or Nimblegen solid-phase or liquid-phase hybridization platform. An adaptor-blocking sequence is also added to the hybridization platform. After the hybridization reaction is completed, the captured sequence is collected by denaturation, etc., and purified to obtain the DNA molecule complementary to the hybridization probe.

Bisulfite Treatment

The captured DNA along with 200 ng fragmented λDNA is subjected to a bisulfite treatment together, for example, an unmethylated cytosine is converted to a uracil using EZ DNA Methylation-Gold Kit™ (ZYMO).

Step 4. PCR amplification and gel-cutting purification

PCR amplification (such as conventional r-Taq or other polymerase amplification) is performed by taking the bisulfite-converted DNA as a template and adding a PCR primer sequence and a HotsTaq DNA polymerase specific for the bisulfite-converted DNA to the PCR system. The amplification product may be purified using following three methods: beads purification, column purification or 2% agarose gel electrophoresis purification. Then, the purified and recycled product is subjected to quantitative PCR (QPCR), and the quantitative product is subjected to sequencing on computer.

Sequencing on Computer and Data Analysis

After subjected to the bisulfite treatment, the captured sequence is subjected to sequencing on a Next-Generation sequencing platform, such as a Solexa sequencing platform using a method of sequence by synthesis. To distinguish the constructed DNA libraries from different samples after sequencing, an index sequence having a length of 6 bp or 8 bp is introduced at one end of a fragment by an adaptor or a PCR primer, which may conveniently subject different libraries to sequencing on computer after directly pooling. A reference sequence is hg18 (a known whole genomic sequence) when performing data analysis.

Concerning the analysis procedure of the raw data obtained by sequencing, reference is made to LI Y et al., *Nature* (2008) (J Wang, et al., (2008). The DNA Methylome of Human Peripheral Blood Mononuclear Cells. *Nature*, 456:60, which is incorporated herein by reference). In practical application, the selection of reference data will be different with different genomic sources studied. The basic analysis procedure may comprise following steps: converting all C to T in a sense strand and converting all G to A in an antisence strand from the data obtained by sequencing; aligning the converted T from C and the converted A from G into hg18 reference genome respectively using a SOAP program (Li R, Li Y., Kristiansen K. & Wang, J. (2008). SOAP: short oligonucleotide alignment program. *Bioinformatics*, 24: 713~714, which is incorporated herein by reference), wherein mismatching of two bases is allowable; calculating uniquely aligned reads into the target region; filtering these reads aligned into the reference sequence by taking Depth>4 as a filtering reference; making the filtered site-methylation information as an actual methylation information obtained by sequencing; and subjecting the filtered site-methylation information to subsequent alignment information analysis.

In contrast to conventionally studied and reported sequencing method of first subjecting the genome to a bisulfite treatment and then performing a sequence capturing, in the present disclosure, a sequence capturing of a specific region is firstly performed, and then a bisulfite treatment is performed. Thus, the methylation status in the sample has not been changed during the sequence capturing process, and consequently the influence of the methylation level of the target region on the sequence capturing efficiency does not need to be considered during the process of designing a capturing probe. All target regions may be captured to verify their methylation information, without having to consider in advance the methylation distribution before designing a chip, and thus the obtained data is more realistic and sufficient. The present disclosure may make the probe designing method in sequence capturing simpler, with high capturing efficiency, and then it may comprehensively and accurately analyze the genomic methylation level.

According to embodiments of the present disclosure, probe designing is simple, which may be based on an existing liquid-phase or solid-phase hybridization chip. The probe may have a length of 60 mer to 120 mer.

According to embodiments of the present disclosure, during the library construction, a methylation index adaptor is ligated before sequence capturing, which may make it possible to simultaneously perform sequence capturing after pooling several samples. The method may not only greatly save cost, but also achieve high-throughput detection of methylation information in a large number of samples.

Additional aspects and advantages of embodiments of present disclosure will be given in part in the following descriptions, become apparent in part from the following descriptions, or be learned from the practice of the embodiments of the present disclosure.

BRIEF DESCRIPTION OF THE DRAWINGS

These and other aspects and advantages of embodiments of the present disclosure will become apparent and more readily appreciated from the following descriptions made with reference to the accompanying drawings, in which.

DETAILED DESCRIPTION

Figure 1:
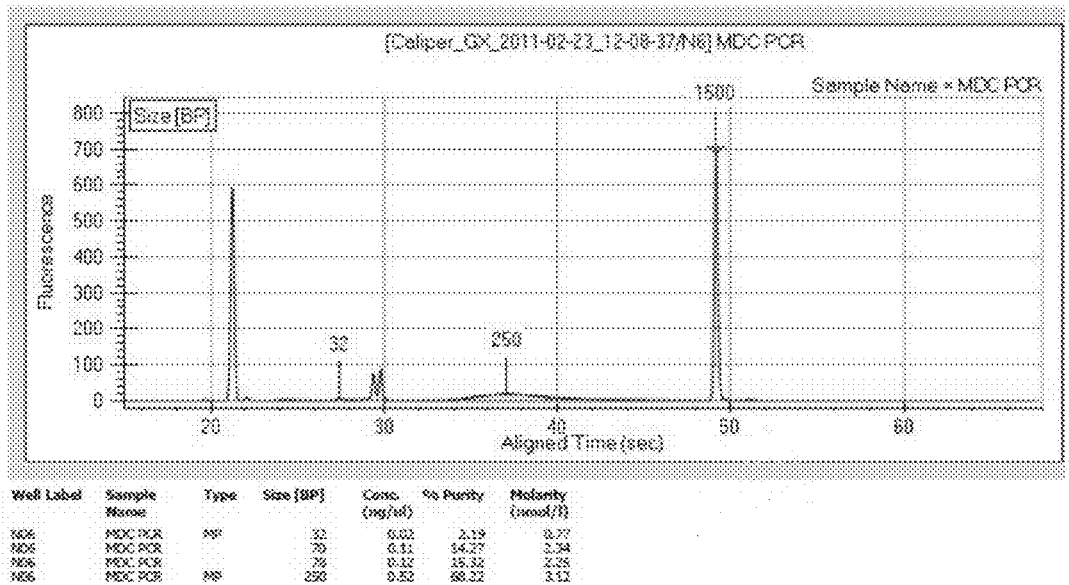
FIG. 1 shows MDC PCR 2100 detection result according to an embodiment of the present disclosure.

Reference will be made in detail to embodiments of the present disclosure. The same or similar elements and the elements having same or similar functions are denoted by like reference numerals throughout the descriptions. The embodiments described herein with reference to drawings are explanatory, illustrative, and used to generally understand the present disclosure. The embodiments shall not be construed to limit the present disclosure.

In addition, terms such as "first" and "second" are used herein for purposes of description and are not intended to indicate or imply relative importance or significance. Thus, features restricted with "first", "second" may explicitly or implicitly comprise one or more of the features. Furthermore, in the description of the present disclosure, unless otherwise stated, the term "a plurality of" refers to two or more.

Reference will be made in detail to embodiments of the present disclosure. It would be appreciated by those skilled in the art that the embodiments are used to illustrate the present disclosure, and should not be considered as limiting the scope of the present disclosure.

In a first aspect of the present disclosure, there is provided a method of constructing a sequencing-library. According to embodiments of the present disclosure, the method may comprise the following steps.

Firstly, a nucleic acid sample is subjected to fragmentation, to obtain a nucleic acid fragment.

According to embodiments of the present disclosure, a sequencing-library may be constructed by the method according to embodiments of the present disclosure. There are no special limitations on a type of the nucleic acid sample which may be used to subsequently determine a methylation information. According to embodiments of the present disclosure, the nucleic acid sample was at least one selected from human genomic DNA, plant genomic DNA or insect genomic DNA. According to embodiments of the present disclosure, there are no special limitations on means for performing the fragmentation; and any chemical or physical methods which may make nucleic acid samples subjected to randomly fragmentation may be used to randomly fragment the nucleic acid sample. According to embodiments of the present disclosure, an ultrasound fragmentation method is preferred for fragmenting the nucleic acid sample. Thus, it is possible to effectively control the length of the obtained nucleic acid fragment. In addition, according to embodiments of the present disclosure, during the process of fragmenting the nucleic acid sample, such as a process of the ultrasound fragmentation, an exogenous genomic DNA is subjected to the same fragmentation process, an exogenous genomic DNA without modification of methylation is preferred, and the exogenous genomic DNA preferably is λDND. Thus, the efficiency of constructing the sequencing-library with the nucleic acid sample and the quality of the final obtained sequencing-library may be improved. According to embodiments of the present disclosure, there are no special limitations on the length of the nucleic acid fragment obtained by fragmenting the nucleic acid sample. According to embodiments of the present disclosure, preferably, the nucleic acid sample is fragmented to obtain a nucleic acid fragment having a length of 200 bp to 300 bp. Thus, the efficiency of constructing sequencing-library with the nucleic acid sample and the quality of the final obtained sequencing-library may be further improved, and the efficiency of subsequent analysis of methylation information may be also further improved. According to embodiments of the present disclosure, the nucleic acid sample in an amount of 5 micrograms or less may be fragmented.

After being obtained, the nucleic acid fragment is ligated to an adaptor, to obtain a nucleic acid fragment ligated to the adaptor. In an embodiment, ligating the nucleic acid fragment to the adaptor may further comprise: end-repairing the nucleic acid fragment, to obtain an end-repaired nucleic acid fragment; adding a base A to the end-repaired nucleic acid fragment at 3'-end, to obtain a nucleic acid fragment having the base A at 3'-end; and ligating the nucleic acid fragment having the base A at 3'-end to a PEI methylated adaptor, to obtain the nucleic acid fragment ligated to the adaptor. According to an embodiment of the present disclosure, the nucleic acid fragment is end-repaired using T4 DNA polymerase, Klenow fragment and T4 polynucleotide kinase. According to an embodiment of the present disclosure, the base A is added to the end-repaired nucleic acid fragment at 3'-end using Klenow fragment (3'-5' exo-) polymerase and dATP. According to an embodiment of the present disclosure, the nucleic acid fragment having the base A at 3'-end is ligated to the PEI methylated adaptor using T4 DNA ligase. Thus, the efficiency of ligating the methylated adaptor may be improved, and then the efficiency of constructing a sequencing-library and the efficiency of determining a methylation information may be improved.

According to an embodiment of the present disclosure, the PEI methylated adaptor is at least one selected from Phos/TCAAGTAGATCGGAAGAGCACACGTCT-GAACTCCAGTCAC (SEQ ID NO:1), and TACACTCTTTCCCTACACGACGCTCTTC-CGATCTACTTGAT (SEQ ID NO:2), wherein all bases C of the PEI methylated adaptor are modified by methylation. The above-mentioned adaptor comprises an index sequence, shown as underlined. The most prominent feature of the Next-Generation sequencing technology is high-throughput, and the Next-Generation sequencing technology may be used for sequencing hundreds of millions of DNA fragments at the same time. Currently, a high-throughput sequencer may produce up to 300 GB of data at one time, equivalent to sequencing 100 times of whole genome of one person. Thus, the sequencing cost may be reduced and the sequencing efficiency may be improved by introducing the index to construct the sequencing-library with a plurality of samples at the same time, and taking full advantages of the sequencing capacity of the high-throughput sequencing platform.

After being ligated the adaptor, the obtained nucleic acid fragment ligated to the adaptor is subjected to sequence capturing using a probe, to obtain a nucleic acid fragment from a predetermined region. Sequence Capture Technology is a technology of selectively enriching a specific region in a genome, comprising: isolating an interested region from the genome by a suitable method and sequencing the isolated target region, which plays a very important role in genomic study with low cost. According to embodiments of the present disclosure, there are no special limitations on a length of the probe. In an embodiment, the probe has a length of 60 mer to 120 mer, preferably, the probe has a length of 120 mer. In addition, according to embodiments of the present disclosure, there are no special limitations on a method of sequence capturing using a probe, for example, the sequence capturing may be performed by a liquid-phase or solid-phase hybridization method. In an embodiment, the sequence capturing may be performed on a liquid-phase hybridization platform. According to an embodiment of the present disclosure, preferably the nucleic acid fragment ligated to the adaptor in an amount of 500 ng to 1000 ng is subjected to sequence capturing. Thus, the efficiency of sequence capturing may be further improved. According to an embodiment of the present disclosure, an adaptor-blocking reagent is added to the hybridization platform, in which the adaptor-blocking reagent has a nucleic acid sequence complementary to the adaptor.

According to embodiments of the present disclosure, a sequence of the probe may be determined based on a type of the selected predetermined region. In some embodiments, the predetermined region is an exon region. Thus, a sequencing-library of the exon region may be effectively constructed and used to subsequently determine the methylation information of the exon region.

After subjected to sequence capturing, the nucleic acid fragment from the predetermined region may be subjected to a bisulfite treatment, to convert an unmethylated cytosine in the nucleic acid fragment from the predetermined region to a uracil, to obtain a converted nucleic acid fragment. According to an embodiment of the present disclosure, the system of subjecting the nucleic acid fragment from the predetermined region to the bisulfite treatment may further comprise adding a fragmented exogenous genomic DNA. According to an embodiment of the present disclosure, the exogenous genomic DNA may be λDNA. Thus, adding the exogenous genomic DNA may play a role in protecting the trace DNA fragment and maximize the reduction of trace DNA damage by the bisulfite treatment.

After completed the bisulfite treatment, the converted nucleic acid fragment is subjected to a PCR amplification, to obtain an amplified product, which may constitute a sequencing-library. According to an embodiment of the present disclosure, the converted nucleic acid fragment is subjected to a PCR amplification, to obtain the amplified product. According to an embodiment of the present disclosure, Taq polymerase is used in the PCR amplification. According to an embodiment of the present disclosure, the PCR amplification is performed using a first primer and a second primer, in which at least one of the first primer and the second primer comprises an index sequence having a length of 6 bp to 8 bp. According to an embodiment of the present disclosure, the first primer has a sequence of:
AATGATACGGCGACCACCGAGATCTA-CACTCTTTCCCTACACGACGCTCTTCCGATCT (SEQ ID NO:3); and the second primer has a sequence of at least one selected from:
CAAGCAGAAGACGGCATACGAGATCT-TGATGTGACTGGAGTTCAGACGTGT-GCTCTTCCGATCT (SEQ ID NO:4); and
CAAGCAGAAGACGGCATACGAGAT-TCAAGTGTGACTGGAGTTCAGACGTGT-GCTCTTCCGATCT (SEQ ID NO5);. Thus, the index sequence (shown as underlined) may be effectively introduced.

A sequencing-library constructed by the method of constructing the sequencing-library according to embodiments of the present disclosure, may be effectively used in determining a methylation information of the nucleic acid sample.

In another aspect of the present disclosure, there is provided a sequencing-library. The sequencing-library is constructed by the method of constructing the sequencing-library above-mentioned. The sequencing-library according to embodiments of the present disclosure may be effectively used in determining the methylation information of the nucleic acid sample. The advantages of the method of constructing the sequencing-library previously described in detail may also apply to the sequencing-library, so a detailed description thereof will be omitted here.

In a further aspect of the present disclosure, there is provided a method of determining a methylation information of a nucleic acid sample. According to embodiments of the present disclosure, the method may comprise: constructing a sequencing-library for the nucleic acid sample according to the above-mentioned method; sequencing the sequencing-library, to obtain a sequencing result; and determining the methylation information of the nucleic acid sample based on the sequencing result. Thus, it is possible to effectively determine the methylation information of the nucleic acid sample by the method of the present disclosure. According to embodiments of the present disclosure, the sequencing is performed using a Next-Generation sequencing platform; preferably, the sequencing is performed using a Solexa sequencing platform. The most prominent feature of the Next-Generation sequencing technology is high-throughput, and the Next-Generation sequencing technology may be used for sequencing hundreds of millions of DNA fragments at the same time. Currently, a high-throughput sequencer may produce up to 300 GB of data at one time, equivalent to sequencing 100 times of whole genome of one person. Thus, the efficiency of determining methylation information may be further improved. The advantages and the characteristics of the sequencing-library and the method of constructing the same previously described in detail may also apply to the method of determining the methylation information of the nucleic acid sample, so a detailed description thereof will be omitted here.

In a further aspect of the present disclosure, there is provided use of the sequencing-library according to embodiments of the present disclosure in determining a methylation information of a nucleic acid sample.

The term "methylation information" used herein should be broadly understood, which may comprise any features regarding methylated bases, such as the content of methylated bases and the distribution of methylated bases (also known as methylation distribution). Thus, in a still aspect of the present disclosure, there is provided a method of determining a methylation distribution information of an exome in a human whole genome. According to embodiments of the present disclosure, the method may comprise: constructing a sequencing-library of the exome for the human whole genome DNA according to the method above-mentioned; sequencing the sequencing-library, to obtain a sequencing result; and determining the methylation distribution information of the exome in the human whole genome based on the sequencing result. It may effectively determine the methylation distribution information of the exome in the human whole genome by the method according to embodiments of the present disclosure. The advantages and the characteristics of the sequencing-library and the method of constructing the same previously described in detail may also apply to the method of determining the methylation distribution information of the exome in the human whole genome, so a detailed description thereof will be omitted here. Recent research (Brenet F et al. 2011; Harder A et al. 2010; Suzuki M M et al. 2008, which are incorporated by reference herein) has found out that: existence of the methylated exon is more prevalent than that of previously appreciated and expected; methylation distributions of the first exon and the first intron are much different from methylation distributions of a downstream exon and a downstream intron; and the methylation level in most downstream regions does not closely relate to gene expression. In short, the relationship of the methylation level surrounding a transcription initial site and the methylation level of the first exon with gene silence is much closer than that of the methylation level of a promoter in upstream region with gene silence. Analyzing the methylation level of exon plays an important role in studying on gene expression.

In addition, the inventors have found out that if a genome is subjected to a bisulfite treatment before performing sequence capturing, difficulties of designing a probe will be significantly increased, and the efficiency and target region coverage of sequence capturing will also be reduced, which limit universal application.

Thus, the present disclosure also provides a high-throughput methylation detection method, which may comprise steps of: selection of probe for sequence capturing, library construction, sequence capturing, bisulfite treatment, sequencing on computer and data analysis. The steps of sequence capturing and bisulfite treatment are performed between the step of ligating adaptor and the PCR amplification step as well as the step of gel-cutting purification of the library construction.

In one embodiment of the present disclosure, the probe used in the high-throughput methylation detection method may be a probe used in the liquid-phase or solid-phase chip hybridization. Preferably the probe has a length of 60 to 120 mer, more preferably the probe has an average length of 120 mer.

In one embodiment of the present disclosure, the step of constructing the library in the high-throughput methylation detection method comprises ligating a methylated index adaptor.

In one embodiment of the present disclosure, following steps of constructing the library are performed before sequence capturing in the high-throughput methylation detection method:

Step 1. Fragmentation of Genomic DNA Sample and Exogenous Genomic DNA

The genomic DNA sample and the exogenous genomic DNA may be from any species, including, but not limited to, human genomic DNA, plant genomic DNA or insect genomic DNA.

Preferably, 5 μg of genomic DNA and λDNA as exogenous genomic DNA are fragmented using physical or chemical methods, preferably using an ultrasound fragmentation method, to obtain a nucleic acid fragment having a preferred length of 200 bp to 300 bp.

Step 2. End-Repairing of Genomic DNA

After recycling and purifying, the nucleic acid fragment is end-repaired using preferred T4 DNA polymerase, Klenow fragment and T4 polynucleotide kinase, to obtain an end-repaired nucleic acid fragment. Then, a base A is added to the end-repaired nucleic acid fragment at 3'-end using preferred Klenow fragment (3'-5' exo-) polymerase and dATP.

Step 3. Ligation of PEI (Paired-End Index) Methylated Adaptor

The nucleic acid fragment having the base A at 3'-end is ligated to an adaptor modified with methylation using a ligase, preferably, the nucleic acid fragment having the base A at 3'-end is ligated to an adaptor modified with methylation at the C site using T4 DNA Ligase, to obtain the nucleic acid fragment ligated to the above adaptor. Then, the nucleic acid fragment ligated to the above adaptor is purified, recycled and subjected to quantification.

In one embodiment of the present disclosure, the PEI methylated adaptor in the high-throughput methylation detection method comprises:

```
PE Index-methylated adaptor 1:
Phos/TCAAGTAGATCGGAAGAGCACACGTCTGAACTCCAGTCAC
(SEQ ID NO: 1, all C sites are modified with
methylation)
and PE Index-methylated adaptor 2:
                                        (SEQ ID NO: 2)
TACACTCTTTCCCTACACGACGCTCTTCCGATCTACTTGAT.
```

In some embodiments, the bases shown as underlined in the sequences of the above adaptors may be varied to produce more and different index primers for various kinds of samples.

In one embodiment of the present disclosure, the step of sequence capturing in the high-throughput methylation detection method comprises:

Subjecting the nucleic acid fragment ligated to the adaptor to sequence capturing on a liquid-phase or solid-phase hybridization platform, preferably the nucleic acid fragment ligated to the adaptor is in an amount of 500 ng to 1000 ng, and the liquid-phase hybridization platform is preferred, and in this hybridization system, an adaptor-blocking may be added at the same time;

After the step of sequence capturing is completed, collecting the captured sequence by denaturation, etc.; and Purifying the collected captured sequence, to obtain DNA molecular complementary to the hybridization probe.

Preferably, exome is subjected to sequence capturing.

In one embodiment of the present disclosure, the adaptor-blocking sequence used in the step of sequence capturing in the high-throughput methylation detection method is a complementary sequence of the PEI methylated adaptor used in the step of ligating adaptor. The adaptor-blocking sequence is selected from a complementary sequence of:

```
PE Index-methylated adaptor 1:
                                      (SEQ ID NO: 1)
Phos/TCAAGTAGATCGGAAGAGCACACGTCTGAACTCCAGTCAC,
or PE Index-methylated adaptor 2:
                                      (SEQ ID NO: 2)
TACACTCTTTCCCTACACGACGCTCTTCCGATCTACTTGAT,
``` in which all C sites of the adaptor are modified with methylation.

In one embodiment of the present disclosure, the step of bisulfite treatment in the high-throughput methylation detection method comprises: subjecting DNA obtained from the sequence capturing step and the fragmented exogenous genomic DNA to bisulfite treatment together. The exogenous genomic DNA is preferably 200 ng of fragmented λDNA.

The present disclosure further provides a high-throughput methylation detection method, which comprises following steps of PCR amplification and gel-cutting purification in library construction after the bisulfite treatment.

PCR amplification is performed by taking the bisulfite-converted DNA as a template and adding a PCR primer sequence and a polymerase to the PCR system. The polymerase used in the PCR amplification comprises a HotsTaq DNA polymerase specific for the bisulfite-converted DNA, a conventional r-Taq or other polymerases, and the HotsTaq DNA polymerase specific for the bisulfite-converted DNA is preferred.

The amplification product is subjected to purification. The purification method includes, but is not limited to, beads purification, column purification and 2% agarose gel electrophoresis purification. Then, the purified and recycled product is subjected to quantitative PCR, and the quantitative product is subjected to sequencing on computer.

In one embodiment of the present disclosure, the PCR amplification step further comprises: introducing an index sequence having a preferred length of 6 bp or 8 bp at one end of a DNA fragment using an adaptor or a PCR primer.

In one embodiment of the present disclosure, the sequence of the PCR primer used in the PCR amplification step of the high-throughput methylation detection method comprises:

```
P1 universal primer:
                                      (SEQ ID NO: 3)
AATGATACGGCGACCACCGAGATCTACACTCTTTCCCTACACGACGCT
CTTCCGATCT, Index 1 primer:
                                      (SEQ ID NO: 4)
CAAGCAGAAGACGGCATACGAGATCTTGATGTGACTGGAGTTCAGACG
TGTGCTCTTCCGATCT,
and Index 2 primer:
                                      (SEQ ID NO: 5)
CAAGCAGAAGACGGCATACGAGATTCAAGTGTGACTGGAGTTCAGACG
TGTGCTCTTCCGATCT.
```

Bases shown as underlined in the above-identified PCR primers may be changed to generate more and different index primers for a plurality of different samples.

In one embodiment of the present disclosure, the step of sequencing on computer and data analysis in the high-throughput methylation detection method comprises: subjecting the sequence obtained from the bisulfate treatment step to sequencing on a sequencing platform, preferably a Next-Generation sequencing platform, more preferably a Solexa sequencing platform; and subjecting the obtained sequencing result to data analysis and comparison.

An additional aspect of the present disclosure provides a sequencing-library constructed by the high-throughput methylation detection method according to the present disclosure.

A still another aspect of the present disclosure provides use of the sequencing-library constructed by the high-throughput methylation detection method according to the present disclosure in high-throughput methylation detection Furthermore, the high-throughput methylation detection method according to the present disclosure is suitable for sequencing exome, preferably used in detecting the methylation distribution of the exome in the human whole genome.

Reference will be made in detail to examples of the present disclosure. It would be appreciated by those skilled in the art that the following examples are explanatory, and can not be construed to limit the scope of the present disclosure. If the specific technology or conditions are not specified in the examples, a step will be performed in accordance with the techniques or conditions described in the literature in the art (for example, referring to J. Sambrook, et al. (translated by Huang P T), *Molecular Cloning: A Laboratory Manual*, 3rd Ed., Science Press) or in accordance with the product instructions. If the manufacturers of reagents or instruments are not specified, the reagents or instruments may be commercially available, for example, from Illumina company.

EXAMPLES

Sequence list (5'->3', index was shown as underlined)

| | |
|---|---|
| PE Index-methylated adapter 1 | Phos/<u>TCAAGT</u>AGATCGGAAGAGCACACGTCTGAACTCCAGTCAC (SEQ ID NO: 1)<br>(all C sites were modified with methylation) |
| PE Index-methylated adapter 2 | TACACTCTTTCCCTACACGACGCTCTTCCGATCT<u>ACTTGAT</u> (SEQ ID NO: 2) (all C sites were modified with methylation) |

-continued

```
Sequence list (5'->3', index was shown as underlined)

P1 universal primer  AATGATACGGCGACCACCGAGATCTACACTCTTTCCCTACACGACGCTCTTCCG
                     ATCT (SEQ ID NO: 3)

Index 1 primer       CAAGCAGAAGACGGCATACGAGATCTTGATGTGACTGGAGTTCAGACGTGTGCT
                     CTTCCGATCT (SEQ ID NO: 4)

Index 2 primer       CAAGCAGAAGACGGCATACGAGATTCAAGTGTGACTGGAGTTCAGACGTGTGCT
                     CTTCCGATCT (SEQ ID NO: 5)
```

DNA Fragmentation

YH genomic DNA from a whole blood sample (Yan Huang genomic DNA from a whole blood sample, from genomic DNA extracted from blood of Chinese adult male) and MDC DNA sample (genomic DNA extracted from human immune cell line) in an initial amount of 5 micrograms were respectively subjected to fragmenting using Covaris-S2 instrument (same with exogenous λDNA). Parameters were set as followings:

| treatment 1 | duty ratio (%) | 10 |
| | intensity | 5 |
| | cycles/impulses | 200 |
| | time (second) | 50 |
| treatment 2 | time (second) | 0 |
| treatment 3 | time (second) | 0 |
| treatment 4 | time (second) | 0 |
| | cycles | 3 |

The fragmented sample was subjected to quality test using 2% agarose gel electrophoresis (the major bands of DNA are centralized between 200 bp to 300 bp, without any contaminations such as protein and RNA), then the qualified sample was purified by QIAquick PCR Purification Kit (Qiagen), and the purified sample was dissolved in 32 μL of an elution buffer.

End-Repairing of Genomic DNA

DNA obtained from the previous step was formulated into a reaction system for end-repairing according to the following composition in a 1.5 mL centrifuge tube:

| DNA sample | 30 μL |
| H$_2$O | 45 μL |
| 10x polynucleotide kinase buffer | 10 μL |
| dNTP solution composition (concentration of each dNTP was 10 mM) | 4 μL |
| T4 DNA polymerase | 5 μL |
| Klenow Fragment | 1 μL |
| T4 polynucleotide kinase | 5 μL |
| Total volume | 100 μL |

The tube was placed on a Thermomixter (Eppendorf) set at 20° C., and allowed the reaction for 30 min. After the reaction was completed, the obtained sample was purified using QIAquick PCR Purification Kit (Qiagen). Then, the purified sample was dissolved in 34 μL, of the elution buffer.

Adding Base a to End-Repaired DNA at 3'-End:

DNA obtained from the previous step was formulated into a reaction system for adding a base A according to the following composition in a 1.5 mL centrifuge tube:

| DNA | 32 μL |
| 10 x blue buffer | 5 μL |
| dATP (1 mM) | 10 μL |
| Klenow (3'-5' exo-) | 3 μL |
| Total volume | 50 μL |

The tube was placed on a Thermomixter (Eppendorf) set at 37° C., and allowed the reaction for 30 min. After the reaction was completed, the obtained sample was purified using MiniElute PCR Purification Kit (Qiagen). Then, the purified sample was dissolved in 16 μL of the elution buffer.

Ligating PEI Methylated Adaptor

DNA obtained from the previous step was formulated into a reaction system for ligating a PEI methylated adaptor according to the following composition:

| DNA | 14 μL |
| 2 x quick ligating buffer | 25 μL |
| PE-index methylated Adapter1 (or 2) | 8 μL |
| T4 DNA ligase | 5 μL |
| Total volume | 50 μL |

The tube was placed on a Thermomixter (Eppendorf) set at 20° C., and allowed the reaction for 15 min. After the reaction was completed, the obtained sample was purified using MiniElute PCR Purification Kit (Qiagen). Then, the purified sample was dissolved in 12 μL of the elution buffer. Then, the dissolved DNA was subjected to quantification assay using Qubit (Invitrogen), and the concentration of DNA was adjusted to 147 ng/μL based on the quantification result by means of concentrating or diluting.

Sequence Capturing:

A hybridization reaction was taken as an example (all reagents come from SureSelect Human All Exon 38M kit):

a. preparation of hybridization reagent A:

| Reagent | Amount for one time sequence capturing |
|---|---|
| SureSelect Hyb #1 | 25 μL |
| SureSelect Hyb # 2 (red cap) | 1 μL |
| SureSelect Hyb # 3 (yellow cap) | 10 μL |
| SureSelect Hyb # 4 | 13 μL |
| Total volume | 49 μL | b. preparation of SureSelect Oligo Library Mix (C):

After being added in aliquots of 5 μL of Oligo Capture Library, a PCR tube was added with 2 μL of diluted RNase Block (a ratio of RNase Block: nuclease-free water=1:3). The PCR tube containing the above reagents was placed on ice.

c. formulation of mixture solution B containing library and Index Block:

| | |
|---|---|
| Library | 3.4 µL 147 ng/µL |
| SureSelect Block #1 | 2.5 µL |
| SureSelect Block #2 | 2.5 µL |
| Index Block | 0.6 µL |
| Total volume | 9 µL |

The PEI methylated adaptor was double-strand DNA. When using single-strand PE-index methylated Adaptor 1 (SEQ ID NO: 1) in the step of ligating the PEI methylated adaptor, the corresponding Index Block had a complementary sequence to the single-strand PE-index methylated Adaptor 1 (SEQ ID NO: 1). When using single-strand PE-index methylated Adaptor 2 (SEQ ID NO: 2) in the step of ligating the PEI methylated adaptor, the corresponding Index Block had a complementary sequence to the single-strand PE-index methylated Adaptor 2 (SEQ ID NO: 2).

The mixture solution B was formulated in the PCR tube, and mixed uniformly by pipetting. Then, the cover of the PCR tube was closed tightly, and the PCR tube was placed onto a PCR instrument. The thermal cycle program was performed under the following conditions:

| Step | Temperature | Time |
|---|---|---|
| Step 1 | 95° C. | 5 min |
| Step 2 | 65° C. | forever | d. The hybridization reagent A was placed onto the PCR instrument at a temperature of 65° C. for at least 5 minutes.

e. The SureSelect Oligo Library Mix (C) was placed onto the PCR instrument at a temperature of 65° C. for at least 2 minutes.

d. The PCR tube was maintained at the temperature of 65° C., 13 µL of hybridization reagent A was quickly transferred to the tube containing SureSelect Oligo Library Mix (C) using a pipette having a volume of 20 µL. Then, the whole mixture solution B containing the library and the Index Block was quickly transferred to the tube containing SureSelect Oligo Library Mix (C) using a pipette having a volume of 20 µL. The tube containing the above three reagents was mixed by slowly pipetting up and down 8 to 10 times using a pipette.

g. The cover of the PCR tube was closed tightly. Then, the hybridization reaction was performed at a temperature of 65° C. (Hot lid temperature was set to 105° C.) for 24 hours.

Sample elution (all reagents come from SureSelect Human All Exon 38M kit):

a. Preparation of Beads

50 µL of DynabeadsM-280 Streptavidin beads were added to a new 1.5 mL centrifuge tube for each hybridization reaction;

The beads were rinsed 3 times using 200 µL of Sure Select Binding buffer; 200 µL of fresh SureSelect Binding buffer was added to the above 1.5 mL centrifuge tube to resuspend the beads.

b. Sample Elution

The centrifuge tubes containing the hybridization mixture solution and the beads were incubated for 30 minutes at room temperature with symmetrically fixed in an instrument BD Clay Adams Nutator Mixer and the like and 360° rotation. After the incubation, the beads in the tubes were shortly spun down for 3 seconds. Then the tubes were subjected to separation using Magnetic Grate, to remove supernatant.

500 µL of fresh SureSelect Binding buffer was added to the tubes to resuspend the beads. Then, the samples in the tubes were firstly mixed for 5 seconds using a vortexer, and then incubated at room temperature for 15 minutes.

Beads rinsing was performed by the following steps to obtain a target fragment.

a) The centrifuge tubes were transferred onto the Magnetic Grate. After standing for 5 to 10 minutes until the mixture solution was clear, the obtained supernatant was removed as much as possible.

b) 500 µL of fresh SureSelect Binding buffer was added to the centrifuge tubes to resuspend the beads. Then, the samples in the centrifuge tubes were mixed for 5 seconds using a vortexer.

c) The obtained samples were incubated at a temperature of 65° C. for 10 minutes using Thermomixer. Then, the centrifuge tubes were firstly shaken up and down by hand to mix the sample, to obtain an even sample, and subsequently were shortly spun down for 3 seconds.

d) Steps a) to c) were repeated 2 times, to clearly remove Wash Buffer#2.

e) After being added with 50 µL of SureSelect elution buffer, the centrifuge tubes were votexed for 5 seconds to resuspend the beads using a Votexer. Then, the samples in the centrifuge tubes were incubated at room temperature for 10 minutes.

f) The centrifuge tubes were transferred onto Dynal Magnetic Grate. The centrifuge tubes were still placed for 5 to 10 minutes until the mixture solution was clear.

g) The eluents containing the samples were respectively transferred to a new 1.5 mL centrifuge tube using a pipette.

h) 50 µL of SureSelect Neutralization Buffer was added to the sequence captured DNA.

i) The salt contained in the sample was removed using 1.8 fold of Ampure Beads.

Bisulfite treatment of sequence captured product added with exogenous DNA

The sequence captured product added with 200 ng of fragmented exogenous λDNA was subjected to bisulfite treatment for 2 hours using EZ DNA Methylation-Gold Kit™ (ZYMO).

Specific steps were shown as followings:

A) Preparation of CT Convention Reagent: CT Conversion Reagent (solid mixture) from the kit, 900 µL of water, 50 µL of M-Dissolving Buffer and 300 µL of M-Dilution Buffer were all added to one new tube. Then, the tube was shaken up and down by hand for 10 minutes or shaken using a shaker at room temperature for 10 minutes to dissolve and mix, to obtain a working solution of CT Convention Reagent.

B) Preparation of M-Wash Buffer: the working solution of M-Wash Buffer was prepared by adding 24 mL of 100% ethanol to the original M-Wash Buffer. After adding ethanol, marking a sing on the cover of the tube using a maker pen indicates the marked tube with working solution.

C) The sequence captured DNA to be converted was added in aliquots to a new PCR tube, and double-distilled water was added to the PCR tube up to 20 µL.

D) After being added with 130 µL of the working solution of CT Conversion Reagent, the sample contained in the PCR tube was mixed by flicking or pipetting.

E) The tube containing the mixed sample was subjected to following treatment using a PCR instrument:
  incubating at 98° C. for 5 minutes;
  incubating at 64° C. for 2.5 hours; and
  performing a next step immediately or being stored at 4° C. (for at most 20 hours).

F) 600 μL of M-Binding Buffer was added to Zymo-Spin IC™ Column which had been put into the Collection Tube provided by the kit.

G) The sample obtained in step E) was filled into the Zymo-Spin IC™ Column containing the M-Binding Buffer. After being tightly closed with a cover, the sample contained in the Collection Tube was mixed by inverting the Collection Tube several times.

H) Then, the tube was centrifuged at a maximum speed (>10,000×g) for 30 seconds, and the obtained liquid passing through the Zymo-Spin IC™ Column was removed.

I) After added with 200 μL of M-Wash Buffer into the Zymo-Spin IC™ Column, the Collection Tube was centrifuged at a maximum speed for 30 seconds.

J) After added with 200 μL of M-Desulphonation Buffer into the Zymo-Spin IC™ Column and incubated at room temperature (about 20° C. to 30° C.) for 15 minutes, the Collection Tube was centrifuged at a maximum speed for 30 seconds.

K) After added with 200 μL of M-Wash Buffer into the Zymo-Spin IC™ Column, the Collection Tube was centrifuged at a maximum speed for 30 seconds. Then, after added with 200 μL of M-Wash Buffer into the Zymo-Spin IC™ Column, the Collection Tube was centrifuged at a maximum speed for 30 seconds.

L) 10 μL of M-Elution Buffer was directly added to the matrix of the Zymo-Spin IC™ Column. Then, after put with the Zymo-Spin IC™ Column containing the M-Elution Buffer, the 1.5 mL centrifuge tube was centrifuged at a maximum speed to elute DNA.

PCR Amplification and Library Selection

DNA obtained from the previous step was formulated to a PCR reaction system according to the following composition:

| | |
|---|---|
| DNA after bisulfite treatment | 10 μL |
| dNTP (2.5 mM) | 2 μL |
| 10 × PCR buffer | 2.5 μL |
| JumpStart ™ Taq DNA Polymerase | 0.3 μL |
| P1 universal primer | 0.5 μL |
| Index 1 or 2 primer | 0.5 μL |
| dH$_2$O | 9.2 μL |
| Total volume | 25 μL |

Condition of PCR reaction:

| | | |
|---|---|---|
| 94° C. | 1 min | |
| 94° C. | 30 s | |
| 58° C. | 30 s | } 18 cycles |
| 72° C. | 30 s | |
| 72° C. | 5 min | |
| 12° C. | forever | |

Then, the obtained amplification product was firstly purified using PCR Purification Kit (Qiagen), and then subjected to 2% agarose gel electrophoresis to separate DNA. Then, a target library having a certain length of DNA was selected and collected by gel-cutting. Then, the collected product was subjected to gel-purifying and DNA-recycling using MiniElute PCR Purification Kit (Qiagen). Then, the obtained library was dissolved in 20 μL of elution buffer.

Library Determination

The conversion efficiency of the genome by bisulfite treatment was detected using TA cloning.

The library production was detected using 2100 Bioanalyzer (Agilent).

The library production was detected by QPCR quantification.

Sequencing and Data Analysis:

The obtained library was subjected to double-end sequencing on a Solexa sequencing platform. The feasibility of the method of analyzing methylation by sequence capturing was analyzed by comparing with the whole genome bisulfite sequencing result and whole exome sequence capturing data from the same samples.

Results:

1. Detection Result of PCR Product Using 2100 Bio Analyzer (Agilent)

Figure 2:
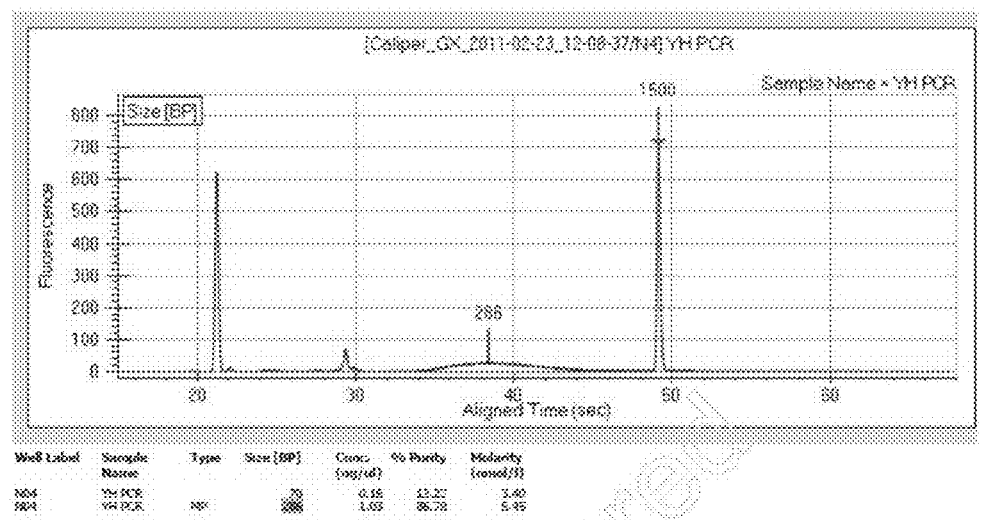
FIG. 2 shows YH PCR 2100 detection result according to an embodiment of the present disclosure.

Detection results of the PCR product using 2100 Bioanalyzer (Agilent) was shown in FIG. 1 and FIG. 2, which indicated that YH genomic DNA from the whole blood sample (Yan Huang genomic DNA from a whole blood sample) and the MDC DNA sample (DNA extracted from mature dendritic cells) in a respective initial amount of 5 micrograms may construct a methylated library which can be used in high-throughput sequencing using a high-throughput Next-Generation sequencer. Combined with the actual sequencing data described below, the analysis result indicted that the method according to embodiment of the present disclosure was practicable, and may be applied to actual research.

2. Result of TA Cloning

TABLE 1

Comparison of the library quality from YH and MDC DNA library construction

| Library | Clone Number Detected | Number of aligned reads | Alignment Ratio (%) | Ratio of methylation (%) | Conversion ratio of unmethylated C |
|---|---|---|---|---|---|
| YH | 36 | 36 | 100 | 89.72 | 99.22 |
| MDC | 41 | 41 | 100 | 91.11 | 99.25 |

36 clones and 41 clones from two respective libraries were selected for quality detection. The results show that the conversion ratios were both above 99%, which suggested that the bisulfite treatment promoted the efficient conversion.

3. Data Analysis 3.1 Comparing with Ratio of Reads Uniquely Aligned into Whole Genome

TABLE 2

Comparison the alignment results from YH, MDC and conventional library construction sequencing results

| Sample | Original sequencing result | | Data Aligned | | Alignment Ratio (%) |
|---|---|---|---|---|---|
| | reads | base (Gb) | reads | base (Gb) | |
| YH | 88568998 | 7.97 | 81305122 | 7.32 | 91.80 |
| MDC | 132592914 | 11.93 | 115583579 | 10.40 | 87.17 |

As can be seen from the above table, the ratios of YH and MDC, being aligned to the sequencing result obtained by the conventional method of constructing the library, were 91.80% and 87.17%, respectively. The efficiency of sequence capturing and conversion ratio of BS were both within a normal range.

3.2 Coverage Distribution

TABLE 3

Coverage distribution of YH and MDC

| Sample coverage | YH | MDC |
| --- | --- | --- |
| target coverage region (%) | 97.49 | 97.25 |
| target coverage region ≥ 4X (%) | 95.20 | 94.67 |
| target coverage region ≥ 10X (%) | 90.21 | 89.16 |
| target coverage region ≥ 20X (%) | 81.24 | 79.37 |
| target coverage region ≥ 30X (%) | 72.37 | 69.74 |
| target coverage region ≥ 40X (%) | 63.88 | 60.58 |
| target coverage region ≥ 50X(%) | 55.92 | 50.53 |

Table 3 showed a distribution under different multipliers of data covering, the current sequencing data intensively distributed in the target region.

Figure 3:
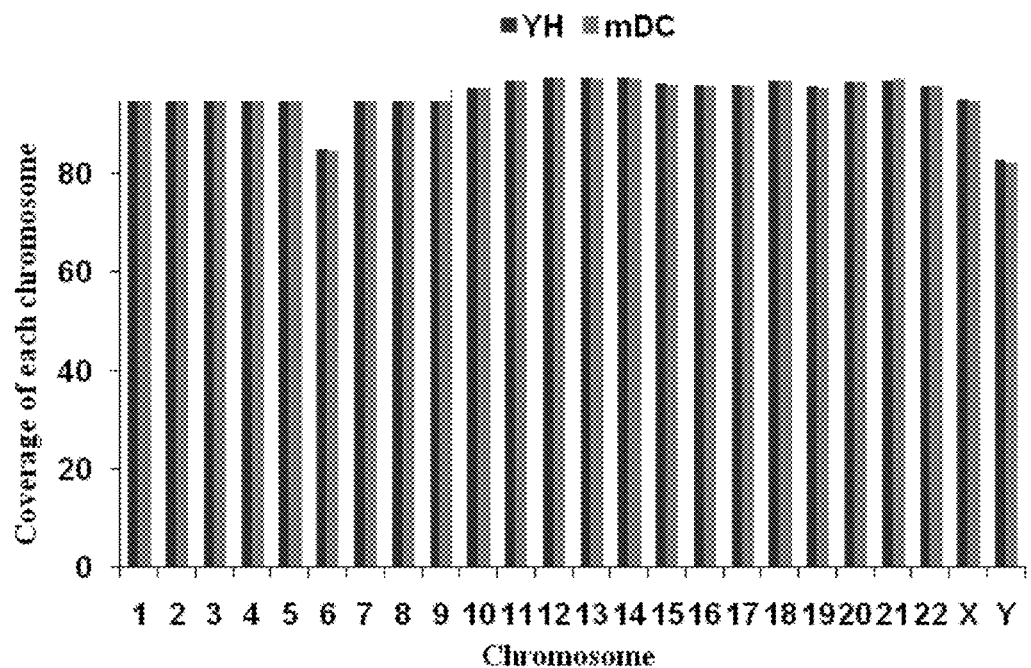
FIG. 3 shows coverage distributions of YH and MDC in each chromosome according to an embodiment of the present disclosure, wherein red column YH represents YH genomic DNA from whole blood, green column MDC represents mature dendritic cells DNA, X-coordinate represents chromosome No., and Y-coordinate represents coverage of each chromosome.

3.2.1 Average Coverage Distribution and Sequencing Depth Distribution of Each Chromosome As can be seen from FIG. 3, the sequencing data substantially may cover the target region of each chromosome.

Figure 4:
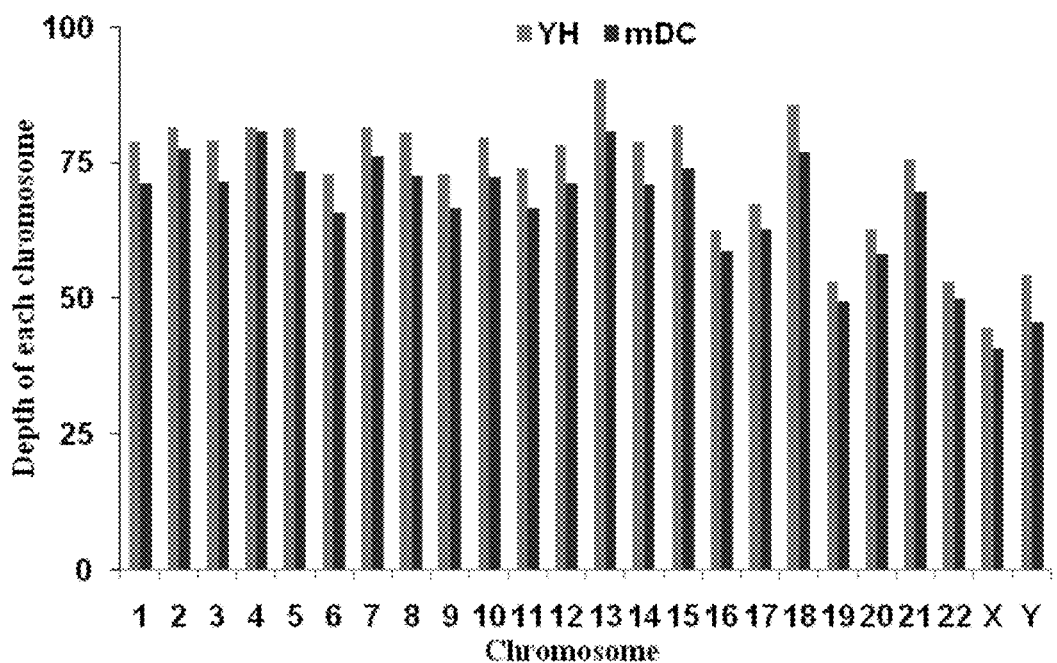
FIG. 4 shows depth distributions of YH and MDC in each chromosome according to an embodiment of the present disclosure, wherein green column YH represents YH genomic DNA from whole blood, red column MDC represents mature dendritic cells DNA, X-coordinate represents chromosome No., and Y-coordinate represents depth of each chromosome.

As can be seen from FIG. 4, the sequencing depths of each chromosome were all around 50×, which may provide more accurate site methylation information during the process of calculating the methylation rate.

Figure 5:
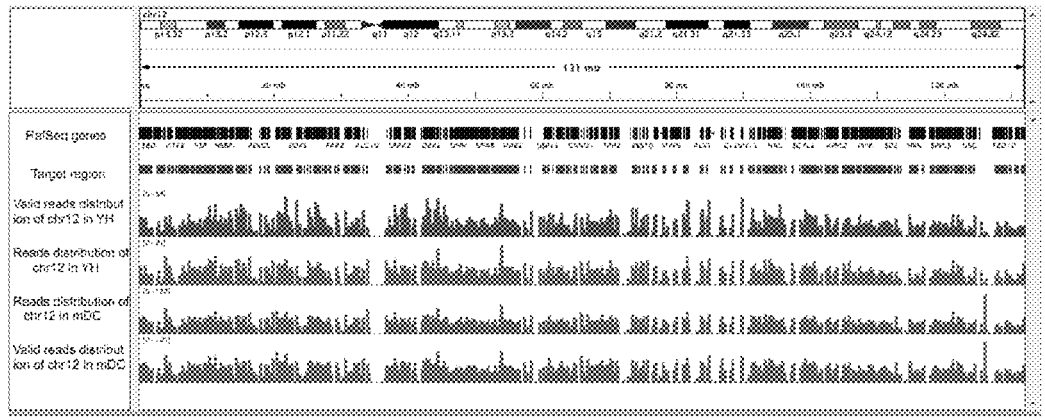
FIG. 5 shows genomic distribution of YH MDC captured fragment according to an embodiment of the present disclosure.

FIG. 5 showed a distribution of the sequence captured data from chromosome 12, which indicated that the obtained data were enriched only within the target region.

3.3 Comparison of Data Correlation

Figure 6:
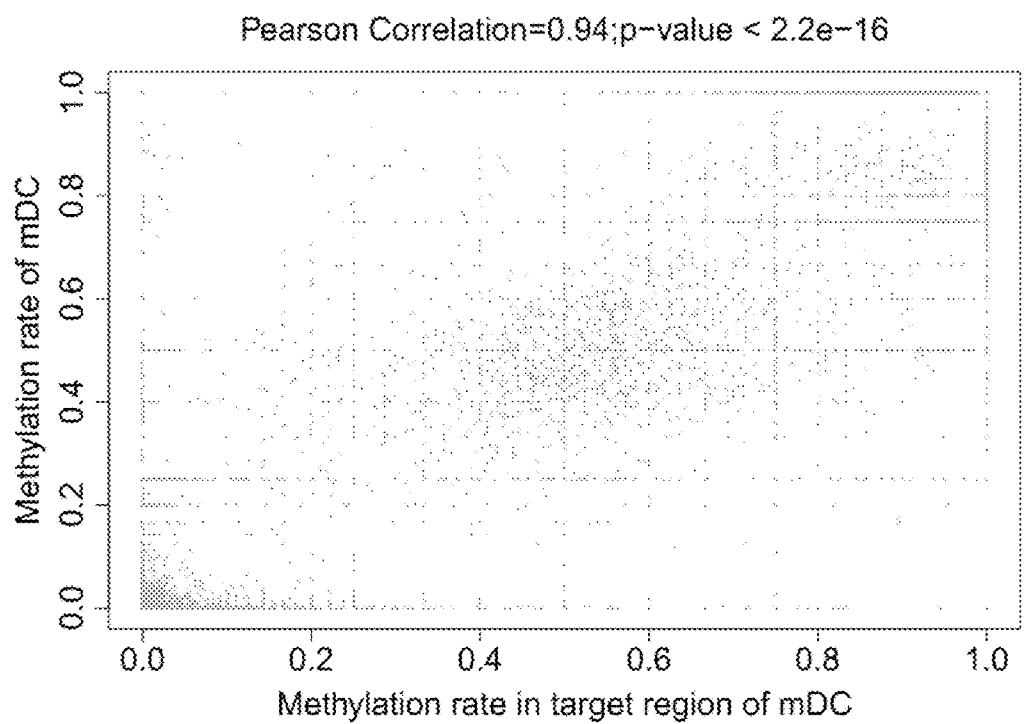
FIG. 6 shows a correlation analysis of sequencing result between a methylation rate of a target region obtained by sequencing capturing in MDC and that of correspondingly whole genome in MDC according to an embodiment of the present disclosure, in which X-coordinate and Y-coordinate represent the methylation rate of the target region obtained by sequence capturing and the methylation rate of the whole genome respectively, and the correlation analysis is Pearson Correlation.
Figure 7:
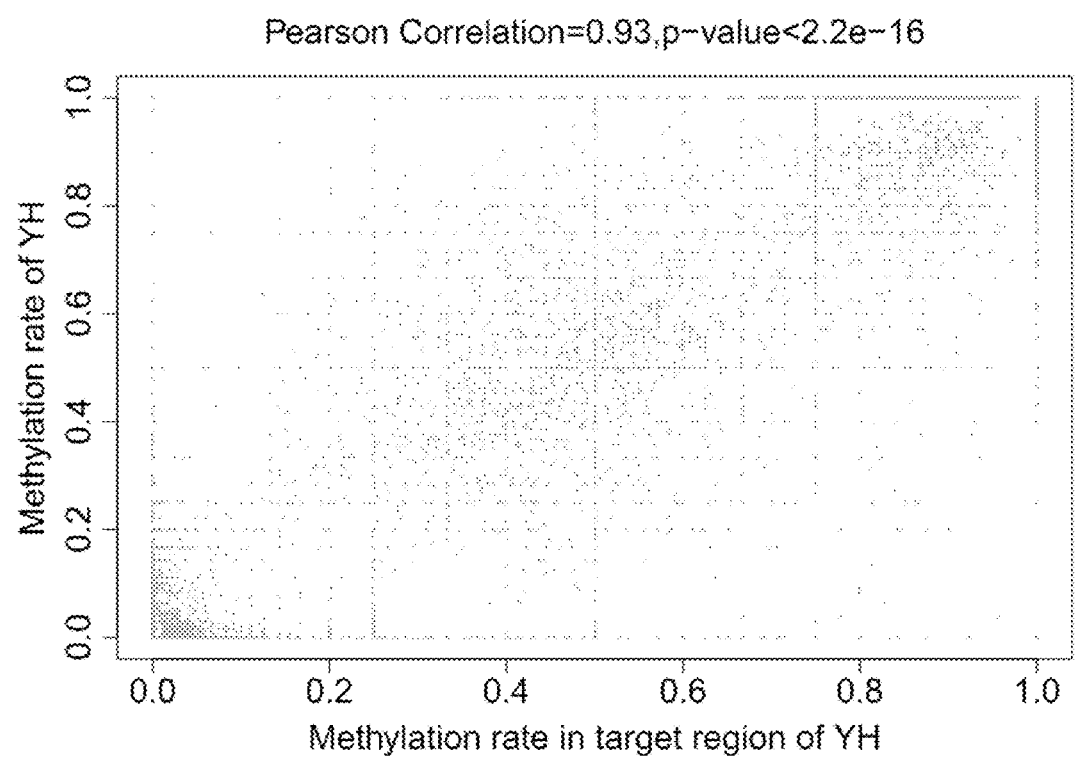
FIG. 7 shows a correlation analysis of sequencing result between a methylation rate of a target region obtained by sequencing capturing in YH and that of correspondingly whole genome in YH according to an embodiment of the present disclosure, in which X-coordinate and Y-coordinate represent the methylation rate of the target region obtained by sequence capturing and the methylation rate of the whole genome respectively, and the correlation analysis is Pearson Correlation.

FIG. 6 and FIG. 7 showed the correlation analysis of sequencing results between the methylation rate of the target region obtained by sequence capturing in MDC and YH respectively, and that of corresponding whole genome in MDC and YH respectively, according to embodiments of the present disclosure. Data used were a methylation ratio distribution with a filtering depth of 10× or more. It can be seen that the methylation rates were substantially consistent at the same site. The Pearson Correlation Coefficient of the MDC sample is 0.94, and the Pearson Correlation Coefficient of the YH sample is 0.93.

As can be seen from the comparison result of the sequencing data obtained by subjecting YH and MDC to specific region capturing to construct the library, with the corresponding data obtained by sequencing the conventional library, from the viewpoints of alignment efficiency, coverage, methylation ratio of each chromosome and correlation, the coverage rate in each aspect is good, methylation rates were also consistent, and the method of the present disclosure may achieve a very deep data volume within a small range. All the above-mentioned results had indicated that studying on high-throughput sequencing of methylation by specific region capturing were practicable, and the method according to the present disclosure decreased the difficulties of designing a probe, increased the feasibility of operation and application, may realize high-throughput and high-accuracy methylation detection of the interested target sequence and region in the whole genome, as well as had characteristics of specificity with low cost and high efficiency.

Industrial Applicability

The methylation information of a nucleic acid sample may be effectively analyzed by the solution according to the present disclosure.

Reference throughout this specification to "an embodiment," "some embodiments," "one embodiment", "another example," "an example," "a specific example," or "some examples," means that a particular feature, structure, material, or characteristic described in connection with the embodiment or example is included in at least one embodiment or example of the present disclosure. Thus, the appearances of the phrases such as "in some embodiments," "in one embodiment", "in an embodiment", "in another example," "in an example," "in a specific example," or "in some examples," in various places throughout this specification are not necessarily referring to the same embodiment or example of the present disclosure. Furthermore, the particular features, structures, materials, or characteristics may be combined in any suitable manner in one or more embodiments or examples.

Although explanatory embodiments have been shown and described, it would be appreciated by those skilled in the art that the above embodiments can not be construed to limit the present disclosure, and changes, alternatives, and modifications can be made in the embodiments without departing from spirit, principles and scope of the present disclosure.

What is claimed is:

1. A method of constructing a sequencing-library, comprising:
fragmenting a nucleic acid sample, to obtain a nucleic acid fragment;
ligating the nucleic acid fragment to an adaptor, to obtain a nucleic acid fragment ligated to the adaptor;
subjecting the nucleic acid fragment ligated to the adaptor to sequence capturing using a probe, to obtain a nucleic acid fragment from a predetermined region;
subjecting the nucleic acid fragment from the predetermined region to a bisulfite treatment, to convert an unmethylated cytosine in the nucleic acid fragment from the predetermined region to a uracil, to obtain a converted nucleic acid fragment; and
amplifying the converted nucleic acid fragment, to obtain an amplified product,
wherein the amplified product constitutes the sequencing-library,
wherein ligating the nucleic acid fragment to the adaptor further comprises:
end-repairing the nucleic acid fragment, to obtain an end-repaired nucleic acid fragment;
adding a base A to the end-repaired nucleic acid fragment at 3'-end to obtain a nucleic acid fragment having the base A at 3'-end; and
ligating the nucleic acid fragment having the base A at 3'-end to a Paired-end Index (PEI) methylated adaptor, to obtain the nucleic acid fragment ligated to the adaptor, wherein the PEI methylated adaptor is at least one selected from:

```
                                                        (SEQ ID NO: 1)
Phos/TCAAGTAGATCGGAAGAGCACACGTCTGAACTCCAGTCAC,
and (SEQ ID NO: 2)
TACACTCTTTCCCTACACGACGCTCTTCCGATCTACTTGAT,
``` wherein all bases C of the PEI methylated adaptor are modified by methylation,
wherein the nucleic acid fragment is end-repaired using T4 DNA polymerase, Klenow fragment and T4 polynucleotide kinase,
wherein the base A is added to the end-repaired nucleic acid fragment at 3'-end using Klenow fragment (3'-5' exo-) polymerase and dATP, and
wherein the nucleic acid fragment having the base A at 3'-end is ligated to the PEI methylated adaptor using T4 DNA ligase.

2. The method of claim 1, wherein the nucleic acid sample is at least one selected from human genomic DNA, plant genomic DNA and insect genomic DNA,
wherein the nucleic acid sample is fragmented by an ultrasound fragmentation method, and
wherein the nucleic acid sample is fragmented to obtain the nucleic acid fragment having a length of 200 bp to 300 bp.

3. The method of claim 1, wherein the nucleic acid fragment is in an amount of 5 micrograms.

4. The method of claim 1, wherein the probe has a length of 60 mer to 120 mer.

5. The method of claim 4, wherein the probe has a length of 120 mer.

23

6. The method of claim 1, wherein the sequence capturing is performed on a liquid-phase hybridization platform.

7. The method of claim 6, wherein the nucleic acid fragment ligated to the adaptor is in an amount of 500 ng to 1000 ng and is subjected to the sequence capturing.

8. The method of claim 6, wherein an adaptor-blocking reagent is added to the hybridization platform,
wherein the adaptor-blocking reagent has a nucleic acid sequence complementary to the adaptor.

9. The method of claim 1, wherein the predetermined region is an exon region.

10. The method of claim 1, further comprising:
adding a fragmented exogenous genomic DNA to a system in which the nucleic acid fragment from the predetermined region is subjected to the bisulfite treatment.

11. The method of claim 10, wherein the exogenous genomic DNA is λDNA.

12. The method of claim 1, wherein the converted nucleic acid fragment is subjected to a PCR amplification, to obtain the amplified product,
wherein Taq polymerase is used in the PCR amplification, and the PCR amplification is performed using a first primer and a second primer,
wherein at least one of the first primer and the second primer comprises an index-sequence having a length of 6 bp to 8 bp,
wherein the first primer has a sequence of AATGATACG-GCGACCACCGAGATCTACACTCTTTC-CCTACACGACGCTCTTCCGATCT (SEQ ID NO:3); and
the second primer has a sequence of at least one selected from:

(SEQ ID NO: 4)
CAAGCAGAAGACGGCATACGAGATCTTGATGTGACTGGAGTTCAGACG
TGTGCTCTTCCGATCT;
and (SEQ ID NO: 5)
CAAGCAGAAGACGGCATACGAGATTCAAGTGTGACTGGAGTTCAGACG
TGTGCTCTTCCGATCT.

13. A method of constructing a sequencing-library, comprising:
fragmenting a nucleic acid sample, to obtain a nucleic acid fragment;
ligating the nucleic acid fragment to an adaptor, to obtain a nucleic acid fragment ligated to the adaptor;
subjecting the nucleic acid fragment ligated to the adaptor to sequence capturing using a probe, to obtain a nucleic acid fragment from a predetermined region;
subjecting the nucleic acid fragment from the predetermined region to a bisulfite treatment, to convert an unmethylated cytosine in the nucleic acid fragment from the predetermined region to a uracil, to obtain a converted nucleic acid fragment;
subjecting the converted nucleic acid fragment to a PCR amplification to obtain an amplified product, wherein Taq polymerase is used in the PCR amplification, and the PCR amplification is performed using a first primer and a second primer,
wherein at least one of the first primer and the second primer comprises an index-sequence having a length of 6 by to 8 bp,

24 wherein the first primer has a sequence of AATGATACG-GCGACCACCGAGATCTACACTCTTTC-CCTACACGACGCTCTTCCGATCT (SEQ ID NO:3); and
the second primer has a sequence of at least one selected from:

(SEQ ID NO: 4)
CAAGCAGAAGACGGCATACGAGATCTTGATGTGACTGGAGTTCAGACGTG
TGCTCTTCCGATCT;
and (SEQ ID NO: 5)
CAAGCAGAAGACGGCATACGAGATTCAAGTGTGACTGGAGTTCAGACGTG
TGCTCTTCCGATCT, wherein the amplified product constitutes the sequencing-library,
wherein ligating the nucleic acid fragment to the adaptor further comprises:
end-repairing the nucleic acid fragment, to obtain an end-repaired nucleic acid fragment;
adding a base A to the end-repaired nucleic acid fragment at 3'-end, to obtain a nucleic acid fragment having the base A at 3'-end; and
ligating the nucleic acid fragment having the base A at 3'-end to a Paired-end Index (PEI) methylated adaptor, to obtain the nucleic acid fragment ligated to the adaptor,
wherein the nucleic acid fragment is end-repaired using T4 DNA polymerase, Klenow fragment and T4 polynucleotide kinase,
wherein the base A is added to the end-repaired nucleic acid fragment at 3'-end using Klenow fragment (3'-5' exo-) polymerase and dATP, and
wherein the nucleic acid fragment having the base A at 3'-end is ligated to the PEI methylated adaptor using T4 DNA ligase.

14. The method of claim 13, wherein the probe has a length of 60 mer to 120 mer.

15. The method of claim 14, wherein the probe has a length of 120 mer.

16. The method of claim 1, wherein the sequence capturing is performed on a liquid-phase hybridization platform.

17. The method of claim 16, wherein the nucleic acid fragment ligated to the adaptor is in an amount of 500 ng to 1000 ng and is subjected to the sequence capturing.

18. The method of claim 16, wherein an adaptor-blocking reagent is added to the hybridization platform,
wherein the adaptor-blocking reagent has a nucleic acid sequence complementary to the adaptor.

19. The method of claim 13, wherein the predetermined region is an exon region.

20. The method of claim 13, further comprising:
adding a fragmented exogenous genomic DNA to a system in which the nucleic acid fragment from the predetermined region is subjected to the bisulfite treatment.

21. The method of claim 20, wherein the exogenous genomic DNA is λDNA.

22. The method of claim 13, wherein the nucleic acid fragment is in an amount of 5 micrograms.

* * * * *

SEQUENCE LISTING

<160> NUMBER OF SEQ ID NOS: 5

<210> SEQ ID NO 1
<211> LENGTH: 40
<212> TYPE: DNA
<213> ORGANISM: Artificial
<220> FEATURE:
<223> OTHER INFORMATION: PE Index_methylated adapter 1

<400> SEQUENCE: 1
tcaagtagat cggaagagca cacgtctgaa ctccagtcac                40

<210> SEQ ID NO 2
<211> LENGTH: 41
<212> TYPE: DNA
<213> ORGANISM: Artificial
<220> FEATURE:
<223> OTHER INFORMATION: PE Index_methylated adapter 2

<400> SEQUENCE: 2
tacactcttt ccctacacga cgctcttccg atctacttga t              41

```
<210> SEQ ID NO 3
<211> LENGTH: 58
<212> TYPE: DNA
<213> ORGANISM: Artificial
<220> FEATURE:
<223> OTHER INFORMATION: P1 universal primer

<400> SEQUENCE: 3
aatgatacgg cgaccaccga gatctacact ctttccctac acgacgctct tccgatct        58

<210> SEQ ID NO 4
<211> LENGTH: 64
<212> TYPE: DNA
<213> ORGANISM: Artificial
<220> FEATURE:
<223> OTHER INFORMATION: Index1 primer

<400> SEQUENCE: 4
caagcagaag acggcatacg agatcttgat gtgactggag ttcagacgtg tgctcttccg       60
atct                                                                   64

<210> SEQ ID NO 5
<211> LENGTH: 64
<212> TYPE: DNA
<213> ORGANISM: Artificial
<220> FEATURE:
<223> OTHER INFORMATION: Index2 primer

<400> SEQUENCE: 5
caagcagaag acggcatacg agattcaagt gtgactggag ttcagacgtg tgctcttccg       60
atct                                                                   64
```